United States Patent [19]

Ottow et al.

[11] Patent Number: 5,132,299

[45] Date of Patent: Jul. 21, 1992

[54] 11β-PHENYL-4,9,15-ESTRATRIENES, THEIR MANUFACTURE AND PHARMACEUTICAL PREPARATIONS CONTAINING SAME

[75] Inventors: Eckhard Ottow; Helmut Hofmeister; Stefan Scholz; Guenter Neef; Walter Elger; Sybille Beier; Krzysztof Chwalisz, all of Berlin, Fed. Rep. of Germany

[73] Assignee: Schering Aktiengesellschaft, Berlin & Bergkamen, Fed. Rep. of Germany

[21] Appl. No.: 458,668

[22] PCT Filed: Jul. 15, 1988

[86] PCT No.: PCT/DE88/00447

§ 371 Date: Jan. 16, 1990

§ 102(e) Date: Jan. 16, 1990

[87] PCT Pub. No.: WO89/00578

PCT Pub. Date: Jan. 26, 1989

[30] Foreign Application Priority Data

Jul. 16, 1987 [DE] Fed. Rep. of Germany ....... 3723788

[51] Int. Cl.$^5$ ............ C07J 1/00; C07J 41/00; A61K 31/565
[52] U.S. Cl. .................. 514/169; 514/179; 552/519; 552/623; 552/646
[58] Field of Search ........... 514/169, 179; 552/540, 552/544, 548, 553, 555, 595, 610, 611, 623, 519, 646

[56] References Cited

U.S. PATENT DOCUMENTS

| 2,530,817 | 11/1950 | Ehrensten | 552/544 |
| 2,940,968 | 6/1960 | Sletzinger et al. | 552/595 |
| 4,536,401 | 8/1985 | Neef et al. | 552/595 |
| 4,609,651 | 9/1986 | Rohde et al. | 514/179 |

FOREIGN PATENT DOCUMENTS

| 51762 | 5/1982 | European Pat. Off. | 514/179 |
| 190759 | 2/1986 | European Pat. Off. | 514/179 |
| 2152378 | 12/1972 | Fed. Rep. of Germany | |
| 8303099 | 9/1983 | World Int. Prop. O. | 514/179 |

OTHER PUBLICATIONS

Grant and Hackh's Chemical Dictionary (1987, New York, McGraw-Hill Book) p. 14.

Primary Examiner—Robert T. Bond
Assistant Examiner—E. C. Ward
Attorney, Agent, or Firm—Millen, White & Zelano

[57] ABSTRACT

New 11β phenyl-4,9,15-estratrienes of formula I

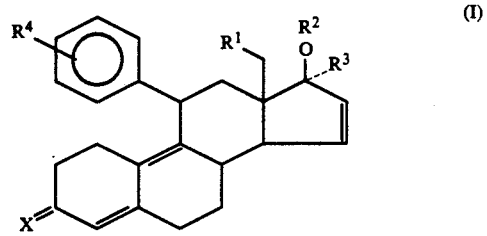

are described, where

X implies an oxygen atom or a hydroxyimino grouping N~OH, $R^1$ stands for a hydrogen atom or a methyl group, $R^2$ implies a hydrogen atom, an alkyl radical or an acyl radical with in each case 1 to 10 carbon atoms, $R^3$ stands for a hydrogen atom, a cyanomethyl group, —$(CH_2)_n CH_2 Z$ where n implies the numbers 0, 1, 2, 3, 4 or 5, Z=—H or —$OR^5$ with $R^5$ having the significance of a hydrogen atom or an alkyl or acyl group with in each case 1 to 10 carbon atoms, or for —$(CH_2)_m$—C≡C—Y where m=0-2 and Y implies a hydrogen, chlorine, fluorine, iodine or bromine atom, an alkyl, hydroxyalkyl, alkoxyalkyl or acyloxyalkyl group with in each case 1 to 10 carbon atoms, $R^4$ represents a straight-chain or branched-chain, saturated or unsaturated hydrocarbon radical with up to 8 carbon atoms which contains the grouping

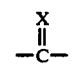

with X having the above significance.

The compounds have antigestagenic and antiglucocorticoid activity.

11 Claims, No Drawings

11β-PHENYL-4,9,15-ESTRATRIENES, THEIR MANUFACTURE AND PHARMACEUTICAL PREPARATIONS CONTAINING SAME

The invention relates to the subject matter characterized in the Patent Claims, i.e. new 11β-phenyl-4,9,15-estratrienes, methods for their production and pharmaceutical preparations containing these compounds.

The compounds in accordance with the invention are characterized by the general formula I

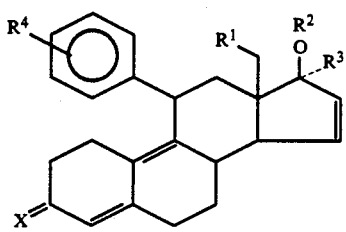

where

X implies an oxygen atom or a hydroxyimino grouping N~OH,

R¹ stands for a hydrogen atom or a methyl group,

R² implies a hydrogen atom, an alkyl radical or an acyl radical with in each case 1 to 10 carbon atoms, R³ stands for a hydrogen atom, a cyanomethyl group, —(CH₂)ₙCH₂Z where n implies the numbers 0, 1, 2, 3, 4 or 5, Z=—H or —OR⁵ with R⁵ having the significance of a hydrogen atom or an alkyl or acyl group with in each case 1 to 10 carbon atoms, or for —(CH₂)ₘ—C≡C—Y where m=0–2 and Y implies a hydrogen, chlorine, fluorine, iodine or bromine atom, an alkyl, hydroxyalkyl, alkoxyalkyl or acyloxyalkyl group with in each case 1 to 10 carbon atoms, R⁴ represents a straight-chain, saturated aliphatic (C₁–C₄)-acyl residue.

The alkyl and acyl contained in R², or the alkyl, acyl or alkoxy groups contained in R⁵ and Y should in each case have 1– carbon atoms, preference being given to the methyl, ethyl, propyl, formyl, acetyl, propionyl, butyryl, benzoyl, methoxy and ethoxy groups.

The acyl residue R⁴ can exhibit up to 4 carbon atoms. Examples that can be cited are the formyl, acetyl, propionyl or butyryl residue. R⁴ is preferably located in the 3- or 4-position of the phenyl ring.

Preferred compounds of the general formula I are:
17-ethinyl-17β-hydroxy-11β-(4-acetylphenyl)-4,9,15-estratrien-3-one
17-(prop-1-inyl)-17β-hydroxy-11β-(4-acetylphenyl)-4,9,15-estratrien-3-one
17-(prop-2-inyl)-17β-hydroxy-11β-(4-acetylphenyl)-4,9,15-estratrien-3-one
17-ethinyl-17β-hydroxy-11β-(4-acetylphenyl)-18-methyl-4,9,15-estratrien-3-one
17-(prop-1-inyl)-17β-hydroxy-11β-(4-acetylphenyl)-18-methyl-4,9,15-estratrien-3-one
17-(prop-2-inyl)-17β-hydroxy-11β-(4-acetylphenyl)-18-methyl-4,9,15-estratrien-3-one
17-methyl-17β-hydroxy-11β-(4-acetylphenyl)-4,9,15-estratrien-3-one
17-butyl-17β-hydroxy-11β-(4-acetylphenyl)-4,9,15-estratrien-3-one
17-(3-hydroxypropyl)-17β-hydroxy-11β-(4-acetylphenyl)-4,9,15-estratrien-3-one
17-(prop-1-inyl)-17β-hydroxy-11β-(4-propionylphenyl)-4,9,15-estratrien-3-one
17-(prop-2-inyl)-17β-hydroxy-11β-(4-propionylphenyl)-4,9,15-estratrien-3-one
17-cyanomethyl-17β-hydroxy-11β-(4-acetylphenyl)-4,9,15-estratrien-3-one The new 11β-phenyl-4,9,15-estratrienes of general formula I are produced in accordance with the invention by the method described in claim 3.

Production of the educts of general formula II starts from 17-keto steroids of general formula III

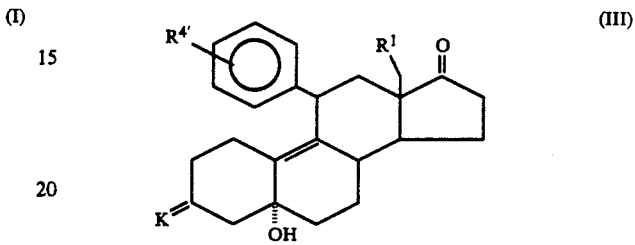

(European Patent Application 86101548.5, Publication-No. 190759) where K implies an acidic hydrolysable keto protection group and R⁴' has the same significance as R⁴ but contains a

grouping instead of

where K¹ stands for K or for a hydrogen atom and a protected hydroxyl group jointly. In particular K represents a keto group blocked in the form of the ketal, thioketal, oxime or methyl oxime.

By e.g. modified Saegusa oxidation [Tetrahedron 42 (1986) 2971] of the corresponding enol compounds of the 17-ketone, the C-15 double bond is introduced into the D-ring. The trimethylsilyl enol ether required for example can be produced by converting the 17-ketone with lithium diisopropylamide in tetrahydrofurane into the corresponding enolate and blocking by trimethylchlorosilane. (Synthesis 1983, 1).

Compounds of general formula II, obtained after conversion of the C-17 keto group into the C-17 substitution pattern, in the significance of R² and R³ ultimately desired in the final product of general formula I

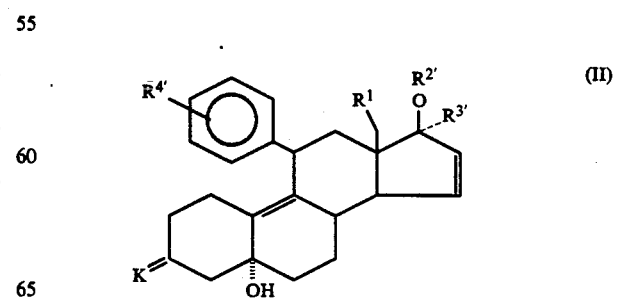

where R¹, R⁴' and K have the above-described meaning, R²' and R³' have the same meaning as R² and R³ and any existing hydroxyl and/or acyl and/or alkyne groups being if necessary protected, are subsequently treated with acid or an acidic ion exchanger to selectively split off water with subsequent production of the 4(5) double bond and at the same time to remove any existing protective groups. This acidic treatment takes place in a manner which is in fact conventional by dissolving the compound of formula II in a solvent miscible with water such as aqueous methanol, ethanol or acetone and allowing catalytic quantities of mineral or sulphonic acids such as hydrochloric acid, sulphuric acid, phosphoric acid, perchloric acid or p-toluene sulphonic acid or an organic acid such as acetic acid to act on the solution long enough for the water to be split off and the protective groups to be removed. The reaction which takes place at temperatures of 0° to 100° C. can also be performed with an acidic ion exchanger. The course of the reaction can be followed by analytical methods, for example by thinlayer chromatography of specimens taken.

If in addition, protective groups which can only be split off in basic surroundings are present, a basic agent is allowed to react before or after acidic treatment.

The protective groups covered in the general formulae II and III by K, $R^{2'}$ and $R^{3'}$ are groups which can be easily split off in acidic surroundings, e.g. the ethylene dioxyketal, ethylene dithio-ketal, 2,2-dimethyltrimethylenedioxy-ketal, hydroxy-imino, methoxy-imino, tetrahydropyranyl, methoxy-methyl or methoxy-ethyl groups. To protect terminal acetylene groups, the trimethylsilyl or tert.-butyldimethylsilyl groups are, for instance, used which can be split off in basic surroundings. If a compound of general formula II is used, in which $K^1$ contains a protected hydroxyl group, this is subsequently converted to the oxofunctional group with an oxidizing agent normal for oxidation of allylic hydroxyl groups such as chromic acid, pyridine, pyridinium dichromate, pyridinium chlorochromate, manganese dioxide, silver carbonate on Celite. The preferred method involves reaction with manganese dioxide at temperatures between −20° C. and +40° C.

The compounds thus obtained of general formula I with X having the significance of an oxygen atom can if required be converted into the oximes (formula I with X having the significance of hydroxy-imino grouping N~OH—where the hydroxyl group can be in the syn or anti position) by reaction with hydroxylamine hydrochloride in the presence of tertiary amines at temperatures between −20° C. and +40° C.

Suitable tertiary bases are for example trimethylamine, triethylamine, pyridine, N,N-dimethylaminopyridine, 1,5-diaza-bicyclo[4.3.0]nonene-5 (DBN) and 1,5-diaza-bicyclo[5.4.0]undecene-5 (DBU) in which connection pyridine is preferred.

Introduction of the substituents $R^2$ and $R^3$ is carried out by the normal methods of C-17 side-chain build-up by nucleophilic addition to the 17-ketone and follow-up reactions ("Terpenoids and Steroids", Specialist Periodical Report, The Chemical Society, London, Vol. 1–12).

The nucleophilic addition of HC≡CU in which U means a protective group, e.g. trimethylsilyl or tert.-butyldimethylsilyl or Y takes place with the aid of a compound of general formula MC≡CU in which U has the above-mentioned significance and M represents an alkali metal.

The metal-organic compound can also be formed in situ and made to react with the 17-ketone. Thus for example acetylene and an alkali metal, in particular potassium, sodium or lithium in the presence of an alcohol or in the presence of ammonia can be allowed to react on the 17- ketone in a suitable solvent. The alkali metal may also be made to react in the form of for example methyl or butyl lithium. Particularly suitable solvents are dialkyl ether, tetrahydrofurane, dioxane, benzene and toluene.

For the production of the 17-chloroethinyl compound, the metal-organic chloroethinyl compound is derived in situ from 1,2-dichloroethylene and an ethereal alkali-metal solution such as e.g. a methyl or butyl lithium solution and allowed to react with the 17-ketone in solvents such as tetrahydrofurane or diethylether.

17-halogen ethinyl compounds can be produced by halogenation of the corresponding ethinyl educt (Angew. Chem. 96, 720 (1984)).

Introduction of 3-hydroxypropine in the 17-position takes place by reaction of the 17-ketone with the dianion of the propargyl alcohol (3-hydroxypropine), for example the dipotassium salt of propargyl alcohol generated in situ, to the 17α-(3-hydroxy-prop-1-inyl)-17β-hydroxy derivative or with metallised derivatives of the 3-hydroxy-propine, for example with 1-lithium-3-(tetrahydro- pyran -2'-yloxy)prop-1-in-1-ide to the 17-[3-(tetrahydropyran-2'-yloxy)prop-1-inyl]-17β-hydroxy derivative.

Introduction of the homologous hydroxyalkyne group takes place in a corresponding manner with homologues of propargyl alcohol.

Introduction of 3-hydroxypropane in the 17-position takes place by reaction of the 17-ketone with metallated derivatives of 3-halogen propanols, where the hydroxyl group in the metallation step is present as an alcoholate (Tetrahedron Letters 1978, 3013) or as a protected functional group to the 17-(3-hydroxypropyl)-17β-hydroxy compound or to the compound protected at the terminal hydroxyl group. The same protective groups are suitable as are mentioned above.

Introduction of the homologous hydroxyalkane groups takes place in a corresponding manner with homologues of the 3-halogen propanols.

Build-up of the 17-cyanomethyl side-chain takes place in a manner which in fact is already familiar from the 17-ketone, for instance by addition of MCH₂CN with M implying an alkali metal, preferably lithium.

Free hydroxyl groups in the 17-position and in the radicals represented by $R^{3'}$ can be esterified or etherified in a manner already known as such.

Apart from this, reference is here made to EP-A 0 190.759 in which numerous compounds are described with the substituents for which claims are made here, with the difference that the compounds described there do not possess a $\Delta^{15}$-double bond.

The new compounds of general formula I are valuable pharmaceutical drugs. They have a strong affinity for the gestagen receptor without themselves possessing gestagenic activity. They are competitive antagonists of progesterone (antigestagens) since they displace the progesterone necessary to maintain pregnancy from the receptor. They are suitable for postcoital fertility control and for inducing abortions.

They can also be employed to counteract hormone-dependent disorders, to provoque menstruation and to induce labour.

In addition, they can be used for treating hormone-dependent carcinomas.

Compounds of general formula I in accordance with the invention also exhibit antiglucocorticoid activity and can thus also be used as drugs in the treatment of corticoid-induced disorders (glaucoma) as well as for combating side effects which may appear in the event of long-term treatment with glucocorticoids (Cushing syndrome). They thus also permit to combat disorders attributable to supersecretion of glucocorticoids, above all obesity, arteriosclerosis, hypertension, osteoporosis and diabetes as well as insomnia.

It has also been found that new compounds of general formula I not only exhibit very good antigestagenic and antiglucocorticoid effects but also that a separation of the two effects can be observed.

The abortifacient activity was determined to define the antigestagenic effect.

The tests were carried out on female rats with a weight of approx. 200 g. After copulation, commencement of pregnancy was ascertained by demonstrating the presence of sperm in vaginal smears. The date on which sperm are detected was considered the 1st day of pregnancy (=d1 p.c.).

The animals were treated with the substance to be tested or the solvent after nidation of the blastocysts from d5 p.c. to d7 p.c. The animals were killed on d9 p.c. and the uteri were checked for implants and points of resorption. Photos were made of all uteri. Lack of implants was considered as abortions.

The test substances were dissolved in a mixture of benzylbenzoate and castor oil (ratio of 1:4). The vehicle volume per individual dose amounted to 0.2 ml. Treatment was subcutaneous (s.c.).

The superiority of the compounds in accordance with the invention is to be shown by comparison of the biological properties of the compounds in accordance with the invention 11$\beta$-(4-acetylphenyl)-17$\beta$-hydroxy-17$\alpha$-(prop-1-inyl)-4,9,15-estratrien-3-one (A), 11$\beta$-(4-acetylphenyl)-17$\beta$-hydroxy-17$\alpha$-(prop-2-inyl)-4,9,15-estratrien-3-one (B)

with 11$\beta$-(4-dimethylaminophenyl)-17$\beta$-hydroxy-17$\alpha$-(prop-1-inyl)-4,9,(10)-estradien-3-one, RU 486 (C) as described in EP-A 0 057 115 and with 11$\beta$-(4-acetylphenyl)-17$\beta$-hydroxy-17$\alpha$-(prop-1-inyl)-4,9-estradien-3-one (D) as can be found in EP-A 0 190 759:

TABLE 1

| | ABORTIVE TEST WITH PREGNANT RATS | |
|---|---|---|
| Substance | Dose mg/animal/day s.c. | Abortion Rate n aborting/n treated rats |
| A | 3.0 | 4/4 |
| | 1.0 | 4/4 |
| | 0.3 | 4/4 |
| B | 3.0 | 4/4 |
| | 1.0 | 4/4 |
| | 0.3 | 4/4 |
| C | 3.0 | 4/4 |
| | 1.0 | 2/4 |
| | 0.3 | 0/4 |
| D | 3.0 | 4/4 |
| | 1.0 | 4/4 |
| | 0.3 | 4/4 |

From Table 1 it can be seen that the compounds (A) and (B) in accordance with the invention are fully abortive at a dose of 0.3 mg, i.e. they are more effective by a factor of 10 than the already known compound RU 486 (C)—a substance which is to be considered as a standard (7th Int. Congress of Endocrinology Jul. 1-7, 1984, Quebec City, Canada; Excerpta Medica, Amsterdam-Oxford-Princeton).

The abortive effect of the substances in accordance with the invention (A) and (B) was also determined using guinea pigs as test animals.

In this connection it was found that (A) and (B) surprisingly possess a strikingly higher abortifacient effect than the structurally related compound (D).

The test results gained from guinea pigs permit more reliable predictions to be made on the abortive activity of the tested compound(s) to be expected in the case of humans than is permitted by the data gained with rats.

To identify the antiglucocorticoid activity, the effect of the substances in accordance with the invention on the tyrosine amino-transferase was determined. The test system is based on measurement of the activity of the liver enzyme tyrosine amino-transferase (TAT) in cultures of RHC (Rat Hepatoma Cells). The enzyme catalyzes the first step in the metabolism of tyrosine and can be induced by glucocorticoids both in the liver and in hepatoma cells. The activity is easy to measure in raw extracts (Granner and Tomkins, (1970) Meth. Enzymol. 15, 633). The enzyme converts the amino group of tyrosine to 2-oxoglutaric acid. Glutaminic acid and p-hydroxy-phenylpyruvate are formed. The more stable p-hydroxy-benzaldehyde is formed from p-hydroxy-phenylpyruvate in an alkaline solution. Its measured absorption lies at 331 nm. The TAT activity in RHC displays a dosage-dependent induction with cortisol (max. activity at $10^{-6}$M) or dexamethasone (max. activity at $10^{-7}$M). The activity can be stimulated by a factor of 4 to 6 above basal value. Simultaneous treatment with corticoid and antiglucocorticoid leads to a decrease in the TAT activity.

The compound in accordance with the invention (A) exhibits in this test 20–50% and the compound in accordance with the invention (B) shows less than 1% of the activity of the standard compound RU 486 (C).

The affinity of the compounds in accordance with the invention to the gestagen receptor is examined with the gestagen receptor binding test. In this test the displacement of the agonist by the antagonist is measured.

Cytosol from rabbit uterus homogenate which contains the receptor molecule (a protein) is used in the test. This binds progesterone with high affinity and low capacity. When these receptors are charged with $^3$H-progesterone in the presence of the unlabeled substance to be tested, the extent to which the $^3$H-progesterone is displaced from the receptor depends on the concentration and binding affinity of the compound to be tested. After separation of the receptor-bound progesterone from the non-bound progesterone, the binding can be determined as a percentage and this value plotted against the log of the molar concentration of the test substance. Characteristic dosage-dependent displacement curves are obtained and the concentration of the test substance can be determined which is required to oust the reference substance completely from the receptor. The competition factor K as a measure of the binding strength is defined as the ratio of the concentration of the test substance to the concentration of the reference substance (progesterone) in which the two compounds exhibit equal displacement of $^3$H-progesterone from the progesterone receptor complex so that a low K-value indicates high binding strength (high affinity).

TABLE 2

| GESTAGEN RECEPTOR BINDING TEST | |
| --- | --- |
| Compound | Rabbit uterus K (gestagen) |
| A | 1.9 |
| B | 2.9 |
| C | 2.9 |
| D | 1.0 |

The table shows that of the test compounds in accordance with the invention quoted representatively, (A) and (B), compound (A) is much stronger in its effect in the gestagen receptor binding test and compound (B) is about the same strength as the standard compound (C).

To sum up it can thus be stated that the compounds in accordance with the invention display a clear dissociation of their antiglucocorticoid and antigestagenic properties both compared with each other and towards the standard compound (C), RU 486, and the structurally similar compound (D).

A further striking property of the compounds in accordance with the invention is their high metabolic stability in comparison with other state-of-the-art compounds. The invention thus also relates to drugs on the basis of the pharmaceutically tolerated compounds of general formula I, i.e. compounds non-toxic in the doses used and, as the case may be, the normal adjuvants and vehicles.

The compounds in accordance with the invention can be processed in accordance with what are in fact familiar methods of galenic medicine to produce pharmaceutical preparations for enteral, percutaneous, parenteral or local application. They can be administered in the form of tablets, coated tablets, gelatine capsules, granulates, suppositories, implants, injectable, sterile, aqueous or oily solutions, suspensions or emulsions, ointments, creams and gels.

The active agent or agents can in this connection be mixed with the adjuvants as are normally encountered in galenic pharmacy, e.g. arabic gum, talcum, starch, mannitol, methylcellulose, lactose, tensides such as Tweens ® or Myrj ®, magnesium stearate, aqueous or non-aqueous vehicles, paraffin derivatives, wetting agents, dispersing agents, emulsifiers, preservatives and aromatic substances to improve the flavour (e.g. essential oils).

The invention thus also involves pharmaceutical compositions which contain at least one compound in accordance with the invention as an active ingredient.

A unit dose contains approx. 1 to 100 mg of the active ingredient(s). The dosage of the compounds in accordance with the invention amounts to approx. 1 to 1000 mg per day in the case of humans.

EXAMPLE 1

17-(Prop-1-inyl)-17$\beta$-hydroxy-11$\beta$-(4-acetylphenyl)-4,9,15-estratrien-3-one 6.1 g of 17-(prop-1-inyl)-11$\beta$-{4-[1,1- (2,2-dimethyltrimethylenedioxy)-ethyl]-phenyl}-3,3-(2,2-dimethyltrimethylenedioxy)-9,15-estradiene-5$\alpha$,17$\beta$-diol is dissolved in 100 ml of 70% aqueous acetic acid and is agitated for 2.5 hours at 50° C. in an inert atmosphere. After having been cooled, the mixture is poured into iced water, neutralized by addition of aqueous ammonia solution and extracted with methylene chloride. The combined organic phases are dried over sodium sulphate and concentrated in vacuo. The residue is chromatographed with a mixture of hexane/acetic ester over silica gel. 3.5 g of the title compound is isolated as white foam.

Crystallisation from acetic ester/acetone yields 3.25 g of the title compound.

Melting point: 162°–164° C.; $[\alpha]_D^{20} = 14.8°$ (CHCl$_3$; c=0.505).

The initial material is prepared by the following method:

a) In an inert atmosphere, 10 ml of diisopropylamine is dissolved in 290 ml of absolute tetrahydofurane at −10° C., mixed with 50 ml of a 1.6 m n-butyllithium solution (hexane). It is then agitated for a further half an hour at 0° C. then cooled again to −10° C., whereafter 13.6 g of 11$\beta$-{4-[1,1-(2,2-dimethyltrimethylenedioxy)-ethyl]-phenyl}-5$\alpha$-hydroxy-3,3-(2,2-dimethyltrimethylenedioxy)-9-estren-17-one (preparation as per European Patent Application 86101548.5, Publication No. 190759, Example 6) dissolved in 150 ml of absolute tetrahydrofurane is added dropwise. After completion of addition, the mixture is stirred for 15 minutes and then 17.2 ml of trimethylchlorosilane is added dropwise. The reaction mixture is then poured over ice-cold saturated sodium bicarbonate solution and the aqueous phase is extracted with acetic ester. The combined organic phases are washed several times with saturated ammonium chloride solution and concentrated in vacuo. The residue is crystallized from 50 ml cf acetonitrile. 13.2 g of 17-trimethylsilyloxy-11$\beta$-{4--1,1-(2,2-dimethyltrimethylenedioxy)-ethyl]-pheny}-]3,3-(2,2-dimethyltrimethylenedioxy)-9,16-estradien-5$\alpha$-ol is obtained.

$^1$H-NMR (CD$_2$Cl$_2$) $\delta$: 4.47 ppm (1H,m,H-16); 4.27 (1H,d J=7.5 Hz, H-11); 1.48 ppm (3H,s, H—CH$_3$); 1.21 (3H,s, H—CH$_3$); 1.01 ppm (3H,s,H—CH$_3$); 0.83 (3H,s, H—CH$_3$); 0.54 ppm (3H,s, H—CH$_3$); 0.5 (3H,s,H-18); 0.15 ppm (9H,s,3, H—CH$_3$ Si).

b) 4.27 g of palladium(II) acetate is dissolved in 150 ml of absolute acetonitrile and mixed with 12.12 g of the compound prepared under a). The reaction mixture is stirred for 16 hours at room temperature, then filtered over silica gel and the filter residue washed well with methylene chloride. The organic phase is concentrated in vacuo and the residue is chromatographed over silica gel. 10 g of 11$\beta$-{4-1,1-(2,2-dimethyltrimethylenedioxy)-ethyl]-phenyl}-5$\alpha$-hydroxy-3,3-(2,2-dimethyltrimethylenedioxy)-9,15-estradien-17-one is isolated as white foam.

$^1$H-NMR (CDCl$_3$) $\delta$: 7.57 ppm (1H,d J=5.5 Hz, H-15); 7.18–7.37 ppm (4H,m,H-aromatic); 6.03 ppm (1H,m,H-16); 4.38 ppm (1H,d J=7.5 Hz, H-11); 1.52 ppm (3H,s,HCH$_3$); 1.25 ppm (3H,s, H—CH$_3$); 1.04 ppm (3H,s,H—CH$_3$); 0.86 ppm (3H,s,H—CH$_3$); 0.75 ppm (3H,s,H—CH$_3$); 0.55 ppm (3H,s,H-18).

c) 500 ml of absolute tetrahydofurane is saturated by passing methyl acetylene through it at 0° C. for 30 minutes. Thereafter 42.2 ml of a 1.6 m solution of n-butyllithium in hexane is added dropwise at 0° to 5° C. After addition the mixture is stirred for 15 minutes. A solution of 9.5 g of the compound prepared under b) in 50 ml of absolute tetrahydrofurane is then added drop for drop. After addition the reaction mixture is stirred for another 60 minutes, poured over iced water and the aqueous phase extracted with acetic ester. The combined organic phases are concentrated in vacuo after they have been dried over sodium sulphate. The residue is chromatographed on aluminium oxide (neutral, stage III) with a mixture of acetic ester/hexane. 9.6 g of 17-(prop-1-inyl)-11$\beta$-{4-[1,1-(2,2-dimethyltrimethylenedioxy)- ethyl]-phenyl}-3,3-(2,2-dimethyltrimethylenedioxy)9,15-estradiene-5α,17β-diol is obtained as white foam.

¹H-NMR (CDCl₃) δ: 7.2-7.4 ppm (4H,m,H-aromatic); 5.95 ppm (1H,d J=6 Hz, H-15); 5.7 ppm (1H dd J=6 and J=2 Hz, H-16); 4.4 ppm (1H,d broad J=8 Hz, H-11); 1.92 ppm (3H,s, H—CH₃—C≡C—); 1.52 ppm (3H,s,H—CH₃); 1.25 ppm (3H,s, H—CH₃); 1.03 ppm (3H,s,H—CH₃); 0.88 ppm (3H,s,H—CH₃); 0.56 ppm (3H,s,H—CH₃); 0.52 ppm (3H,s,H-18).

EXAMPLE 2

17-(Prop-2-inyl)-17β-hydroxy-11β-(4-acetylphenyl)-4,9,15-estratrien-3-one 350 mg of 17-(3-trimethylsilyl-prop-2-inyl)-17β-hydroxy-11β-(4-acetylphenyl)-4,9,15-estratrien-3-one is dissolved in methanol and stirred at 23° C. for 1.5 hours after addition of 387 mg of potassium carbonate. This is poured into water and extracted with acetic ester. The combined organic phases are dried over sodium sulphate and concentrated in vacuo. The residue is chromatographed with a mixture of hexane/acetic ester over silica gel. 205 mg of the title compound is isolated as white foam. Crystallisation from ether yields 176 mg of the title compound.

Melting point: 152°-154° C.; $[\alpha]_D^{20} = 156.8°$ (CHCl₃; c=0.500)

The initial material is prepared in the following way:

a) In an inert atmosphere 1.17 g of 1-(trimethylsilyl)-1-propine is dissolved in 500 ml of absolute tetrahydrofurane at −5° C. and mixed with 6.8 ml of a 1.6 m solution (hexane) of n-butyllithium. The mixture is then stirred for one hour at this temperature and then cooled to −78° C., and 1.5 g of the compound prepared in accordance with Example 1b) dissolved in 200 ml of tetrahydrofurane is added drop by drop. After completion of the addition, the mixture is stirred for 15 hours at 23° C. Therafter the mixture is poured over cold saturated ammonium chloride solution and the aqueous phase is extracted with acetic ester. The combined organic phases are first washed with saturated sodium bicarbonate solution then with saturated common salt solution and concentrated in vacuo. The residue is chromatographed with a mixture of hexane/acetic ester over neutral aluminium oxide (activity 3). 1.22 g of 17-(3-trimethylsilyl-prop-2-inyl)-11β-{4-[1,1-(2,2-dimethyltrimethylenedioxy)-ethyl]-phenyl}-3,3-(2,2-dimethyltrimethylenedioxy)-9,15-estradiene-5α,17β-diol is obtained.

¹H-NMR (CD₂Cl₂)δ: 7.23 ppm, 7.29 ppm (4H, AA'BB'system, J=9 Hz, H-aromatic); 5.93 ppm (1H,d J=6 Hz, H-16); 5.69 ppm (1H,dd J=6 and 4 Hz, H-15); 4.38 ppm (1H, d broad J=8 Hz, H-11); 4.27 ppm (1H,s,OH); 2.45 ppm (2H,s,CH₂—C≡C—); 1.49 ppm (3H,s,H—CH₃); 1.22 ppm (3H,s,H—CH₃); 1.04 ppm (3H,s,H—CH₃); 0.86 ppm (3H,s,H—CH₃); 0.58 ppm (6H,s,H-18 and H—CH₃); 0.18 ppm (9H,s,3×H—CH₃Si).

b) 1.2 g of the compound prepared under a) is dissolved in 15 ml of 70% aqueous acetic acid and stirred at 50° C. for 15 minutes in an inert atmosphere. After the mixture has cooled it is poured into saturated sodium bicarbonate solution and extracted with acetic ester. The combined organic phases are dried over sodium sulphate and concentrated in vacuo. The residue is chromatographed with a mixture of hexane/acetic ester over silica gel. After crystallisation from ether, 582 mg of 17-(3-trimethylsilyl-prop-2-inyl )-17β-hydroxy-11β-(4-acetylphenyl)-4,9,15-estratrien-3-one is obtained as white crystals.

Melting point: 186°-189° C.; $[\alpha]_D^{20}=123.6°$ (CHCl₃; c=0.500).

We claim:

1. An 11β-phenyl-4,9,15-estratriene of formula I

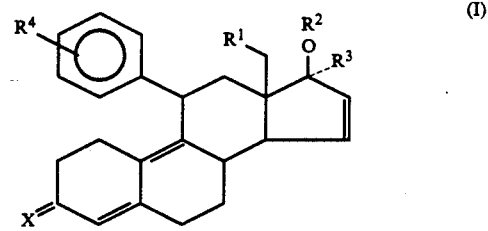

wherein

X is oxygen or hydroxyimino, N~OH;

R¹ is hydrogen or methyl;

R² is hydrogen, alkyl, or acyl with in each case 1-10 carbon atoms;

R³ is hydrogen, cyanomethyl, —(CH₂)ₙCH₂Z, where n is 0, 1, 2, 3, 4, or 5, Z=—H or —OR⁵ with R⁵ being hydrogen, alkyl, or acyl with in each case 1-10 carbon atoms, or —(CH₂)ₘ—C≡C—Y, where m=0-2 and Y is hydrogen, chlorine, fluorine, iodine, or bromine, alkyl, hydroxyalkyl, alkoxyalkyl, or acyloxyalkyl with in each case 1-10 carbon atoms; and R⁴ is a hydrocarbon radical with up to 8 carbon atoms which contains the grouping

with X having the above meaning.

2. 17-ethinyl-17β-hydroxy-11β-(4-acetylphenyl)-4,9,15-estratrien-3-one 17-(prop-1-inyl)-17β-hydroxy-11β-(4-acetylphenyl)-4,9,15-estratrien-3-one 17-(prop-2-inyl)-17β-hydroxy-11β-(4-acetylphenyl)-4,9,15-estratrien-3-one 17-ethinyl-17β-hydroxy-11β-(4-acetylphenyl)-18-methyl-4,9,15-estratrien-3-one 17-(prop-1-inyl)-17β-hydroxy-11β-(4-acetylphenyl)-18-methyl-4,9,15-estratrien-3-one 17-(prop-2-inyl)-17β-hydroxy-11β-(4-acetylphenyl)-18-methyl-4,9,15-estratrien-3-one 17-methyl-17β-hydroxy-11β-(4-acetylphenyl)-4,9,15-estratrien-3-one 17-butyl-17β-hydroxy-11β-(4-acetylphenyl)-4,9,15-estratrien-3-one 17-(3-hydroxypropyl)-17β-hydroxy-11β-(4-acetylphenyl)-4,9,15-estratrien-3-one 17-(prop-1-inyl)-17β-hydroxy-11β-(4-propionylphenyl)-4,9,15-estratrien-3-one 17-(prop-2-inyl)-17β-hydroxy-11β-(4-propionylphenyl)-4,9,15-estratrien-3-one 17-cyanomethyl-17β-hydroxy-11β-(4-acetylphenyl)-4,9,15-estratrien-3-one.

3. A pharmaceutical preparation comprising a pharmaceutically compatible vehicle and a compound in accordance with claim 1.

4. A pharmaceutical preparation comprising pharmaceutically compatible vehicle and a compound in accordance with claim 2.

5. A method of effecting antigestagenic activity comprising administering a compound in accordance with claim 1 to a host.

6. A method of effecting antiglucocorticoid activity comprising administering a compound in accordance with claim 1 to a host.

7. A method of effecting antigestagenic activity comprising administering a compound in accordance with claim 2 to a host.

8. A method of effecting antiglucocorticoid activity comprising administering a compound in accordance with claim 2 to a host.

9. A method of effecting both antigestagenic and antiglucocorticoid activity comprising administering a compound in accordance with claim 1 to a host.

10. A method of effecting both antigestagenic and antiglucocorticoid activity comprising administering a compound in accordance with claim 2 to a host.

11. A compound in accordance with claim 1, wherein $R^2$ and $R^5$ and Y are selected from methyl, ethyl, propyl, formyl, acetyl, propionyl, butyryl, benzoyl, methoxy, or ethoxy groups.

* * * * *